US012102373B2

(12) United States Patent
Kato

(10) Patent No.: US 12,102,373 B2
(45) Date of Patent: Oct. 1, 2024

(54) GENERATOR

(71) Applicant: OLYMPUS CORPORATION, Hachioji (JP)

(72) Inventor: Gen Kato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1106 days.

(21) Appl. No.: 16/935,706

(22) Filed: Jul. 22, 2020

(65) Prior Publication Data

US 2020/0345406 A1 Nov. 5, 2020

Related U.S. Application Data

(63) Continuation of application No. PCT/JP2018/002124, filed on Jan. 24, 2018.

(51) Int. Cl.
*A61B 18/12* (2006.01)
*A61B 18/00* (2006.01)

(52) U.S. Cl.
CPC ............... *A61B 18/1206* (2013.01); *A61B 2018/00607* (2013.01); *A61B 2018/0063* (2013.01); *A61B 18/1233* (2013.01); *A61B 2018/124* (2013.01); *A61B 2018/1246* (2013.01); *A61B 2018/1286* (2013.01)

(58) Field of Classification Search
CPC ........ A61B 2018/1286; A61B 18/1206; A61B 18/12
See application file for complete search history.

(56) References Cited

U.S. PATENT DOCUMENTS

| | | | | |
|---|---|---|---|---|
| 2008/0082094 | A1* | 4/2008 | McPherson | ........ A61B 18/1206 606/34 |
| 2015/0008739 | A1* | 1/2015 | Albu | ..................... H02M 5/458 307/31 |
| 2016/0120591 | A1* | 5/2016 | Smith | ................ A61B 18/1206 606/34 |

FOREIGN PATENT DOCUMENTS

| | | |
|---|---|---|
| JP | 2008-80134 A | 4/2008 |
| JP | 2015-515343 A | 5/2015 |

(Continued)

OTHER PUBLICATIONS

Aug. 6, 2020 Translation of International Preliminary Report on Patentability issued in International Application No. PCT/JP2018/002124.

(Continued)

*Primary Examiner* — Jaymi E Della
(74) *Attorney, Agent, or Firm* — Oliff PLC

(57) ABSTRACT

A generator includes first, second, and third inductors and a capacitor. The first inductor is formed by a primary coil of a transformer. The second inductor is formed by a first secondary coil of the transformer. The second inductor is connected between a first contact and a second contact. The first and the second contacts are connected to a surgical instrument. The third inductor is formed by a second secondary coil of the transformer continuously connected to the first secondary coil. The third inductor is connected between the second contact and a third contact. A polarity of the second contact with respect to the third contact coincides with a polarity of the first contact with respect to the second contact of the second inductor. The capacitor is connected between the third contact and ground. An inductance of the third inductor and a capacitance of the capacitor are adjusted.

7 Claims, 12 Drawing Sheets

(56) References Cited

FOREIGN PATENT DOCUMENTS

| | | |
|---|---|---|
| JP | 2017-536170 A | 12/2017 |
| WO | 2011/044338 A2 | 4/2011 |

OTHER PUBLICATIONS

Dec. 5, 2022 Office Action issued in Chinese Patent Application No. 201880087240.6.

Apr. 24, 2018 International Search Report issued in International Patent Application No. PCT/JP2018/002124.

* cited by examiner

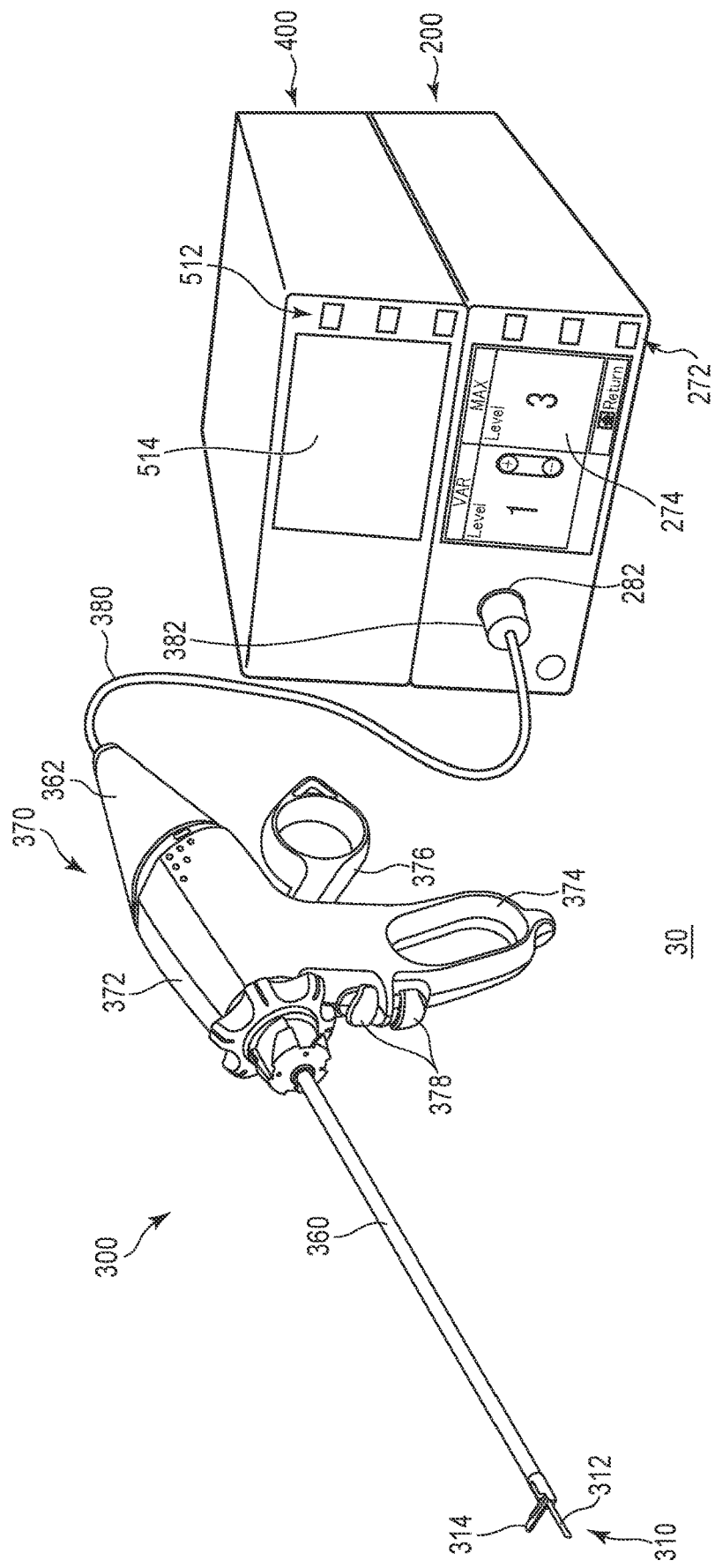
F I G. 5

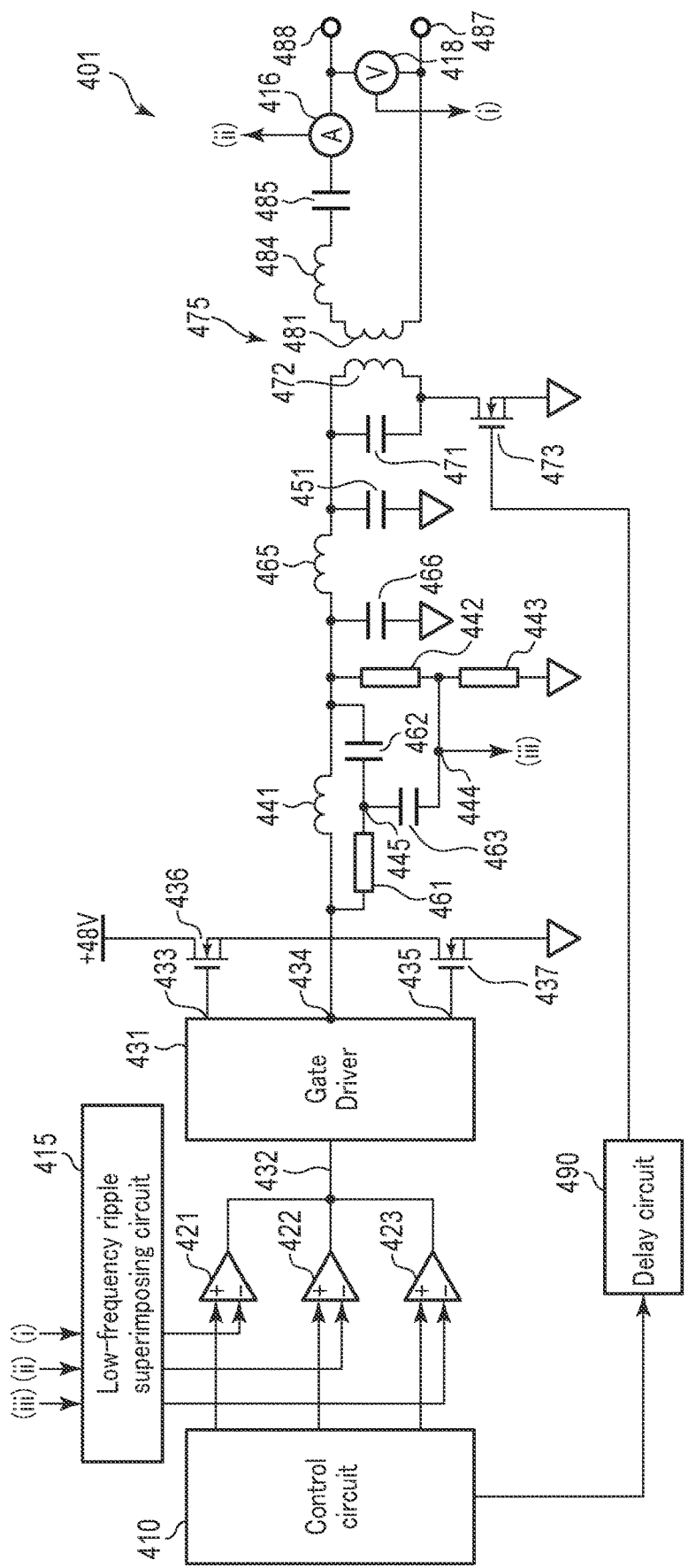
F I G. 13

GENERATOR

CROSS-REFERENCE TO RELATED APPLICATIONS

This application is a Continuation Application of PCT Application No. PCT/JP2018/002124, filed Jan. 24, 2018, the entire contents of which are incorporated herein by reference.

FIELD

Embodiments described herein relate to a generator.

BACKGROUND

There exists a treatment instrument configured to treat a living tissue by inputting various types of energy thereto. There also exists a generator configured to supply power to such a treatment instrument. This generator needs to be designed to prevent, even in the event of a malfunction, flow of a leak current in excess of a predetermined value to a patient.

SUMMARY

According to a first aspect, a generator includes a first inductor, a second inductor, a third inductor, and a capacitor. The first inductor is a primary coil of a transformer. The second inductor is a first secondary coil of the transformer. The second inductor is connected between a first contact and a second contact. The first contact and the second contact each is connected to a surgical instrument. The third inductor is a second secondary coil of the transformer. The third inductor is connected between the first contact and a third contact. A polarity of the second contact with respect to the third contact coincides with a polarity of the first contact with respect to the second contact of the second inductor. The capacitor is connected between the third contact and ground. An inductance of the third inductor and a capacitance of the capacitor are adjusted in such a manner that a potential of the second contact is equal to or less than a predetermined value.

According to a second aspect, a surgical system includes a surgical instrument and a generator. The generator includes a first inductor, a second inductor, a third inductor, and a capacitor. The first inductor is a primary coil of a transformer. The second inductor is a first secondary coil of the transformer. The second inductor is connected between a first contact and a second contact. The first contact and the second contact each is connected to a surgical instrument. The third inductor is a second secondary coil of the transformer. The third inductor is connected between the first contact and a third contact. A polarity of the second contact with respect to the third contact coincides with a polarity of the first contact with respect to the second contact of the second inductor. The capacitor is connected between the third contact and ground. An inductance of the third inductor and a capacitance of the capacitor are adjusted in such a manner that a potential of the second contact is equal to or less than a predetermined value.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 5 is a schematic view showing an exemplary appearance of a surgical system according to a second embodiment.

FIG. 13 is a schematic view showing an exemplary configuration of a drive circuit including a low-frequency ripple generating circuit in a second example.

DETAILED DESCRIPTION

First Embodiment

<Configuration of Ultrasonic Surgical System>

Figure 1:
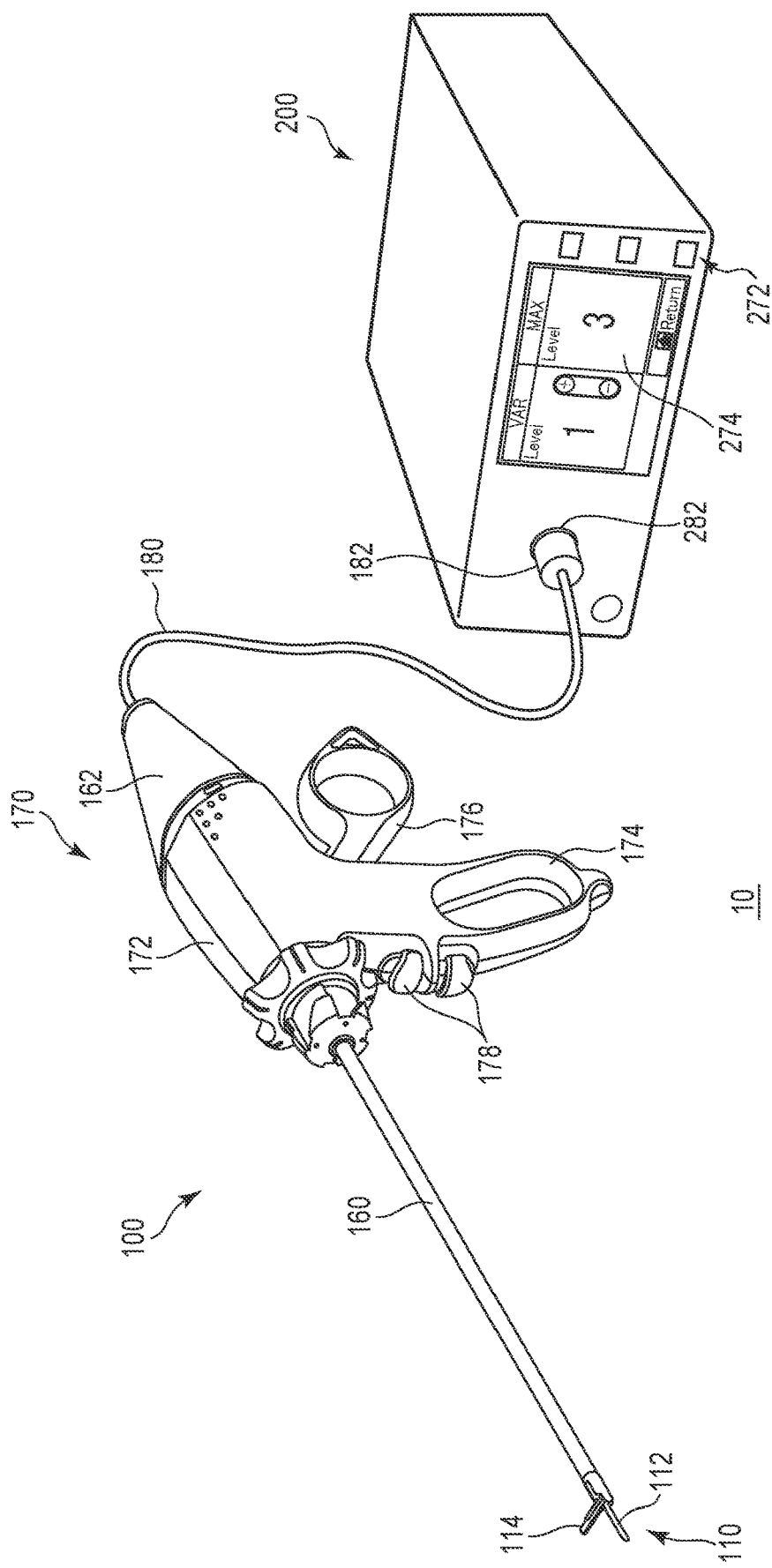
FIG. 1 is a schematic view showing an exemplary appearance of an ultrasonic surgical system according to a first embodiment.

A first embodiment will be described with reference to the accompanying drawings. FIG. 1 is a schematic view of an ultrasonic surgical system 10 according to the present embodiment. The ultrasonic surgical system 10 includes an ultrasonic surgical instrument 100 and a generator 200. The generator 200 supplies power to the ultrasonic surgical instrument 100.

The ultrasonic surgical instrument 100 includes a shaft 160, a treatment portion 110 provided in a distal end of the shaft 160, and an operation unit 170. For convenience of explanation, hereinafter, a side in which the treatment portion 110 is provided will be referred to a distal side, whereas a side in which the operation unit 170 is provided will be referred to as a proximal side. The ultrasonic surgical system 10 is configured to grasp a treatment target with the treatment portion 110. Examples of the treatment target include a living tissue such as a vessel.

The treatment portion 110 is provided with a pair of grasping pieces. One of those grasping pieces will be referred to as a first grasping piece 112, whereas the other of them will be referred to as a second grasping piece 114. The second grasping piece 114 is displaced with respect to the first grasping piece 112. As a result, the treatment portion 110 is opened and closed in such a manner as to grasp a treatment target. The first grasping piece 112 is mechanically connected to an ultrasonic transducer 162 provided in the proximal side of the operation unit 170. The first grasping piece 112 vibrates in its longitudinal direction in accordance with vibration of the ultrasonic transducer 162. With the use of friction heat caused by the vibration described above, the ultrasonic surgical system 10 coagulates, cuts, or seals a living tissue such as a vessel grasped with the treatment portion 110.

The operation unit 170 includes a main body 172, a fixed handle 174, a movable handle 176, and an output switch 178. The fixed handle 174 is fixed to the main body 172. The movable handle 176 is displaced with respect to the fixed handle 174. The movable handle 176 is connected to a wire or a rod inserted through the inside of the shaft 160. This wire or rod is connected to the second grasping piece 114. The operation on the movable handle 176 is transmitted to the second grasping piece 114. The second grasping piece 114 is displaced with respect to the first grasping piece 112 in accordance with the operation on the movable handle 176. As a result, the first grasping piece 112 and the second grasping piece 114 open and close.

The proximal side of the ultrasonic transducer 162 is connected to one end of a cable 180. The other end of the cable 180 is provided with a plug 182. The plug 182 is configured to be inserted into a socket 282 of the generator 200. By the plug 182 being inserted into the socket 282, the ultrasonic surgical instrument 100 is connected to the generator 200.

The generator 200 controls the operation of the ultrasonic surgical instrument 100, and supplies a power to the ultrasonic surgical instrument 100. The generator 200 includes an input unit 272 and a touch screen 274. The input unit 272 includes a button switch, etc. The touch screen 274 includes, for example, a liquid crystal display (LCD) and a touch panel.

The output switch 178 provided in the operation unit 170 includes, for example, two buttons. These buttons are pressed to exert ultrasonic vibration on a treatment target grasped with the treatment portion 110. When detecting any of the buttons being pressed, the generator 200 applies AC voltage to the ultrasonic transducer 162 provided in the operation unit 170. At this time, the ultrasonic transducer 162 vibrates. By this vibration being transmitted, the first grasping piece 112 vibrates. As a result, a living tissue grasped with the treatment portion 110 is treated. The ultrasonic surgical instrument 100 is configured in such a manner that, for example, an output level differs depending on which one of the two buttons is pressed. The ultrasonic surgical system 10 may include a foot switch having an equivalent function to that of the output switch 178.

<Configuration of Drive Circuit>

Figure 2:
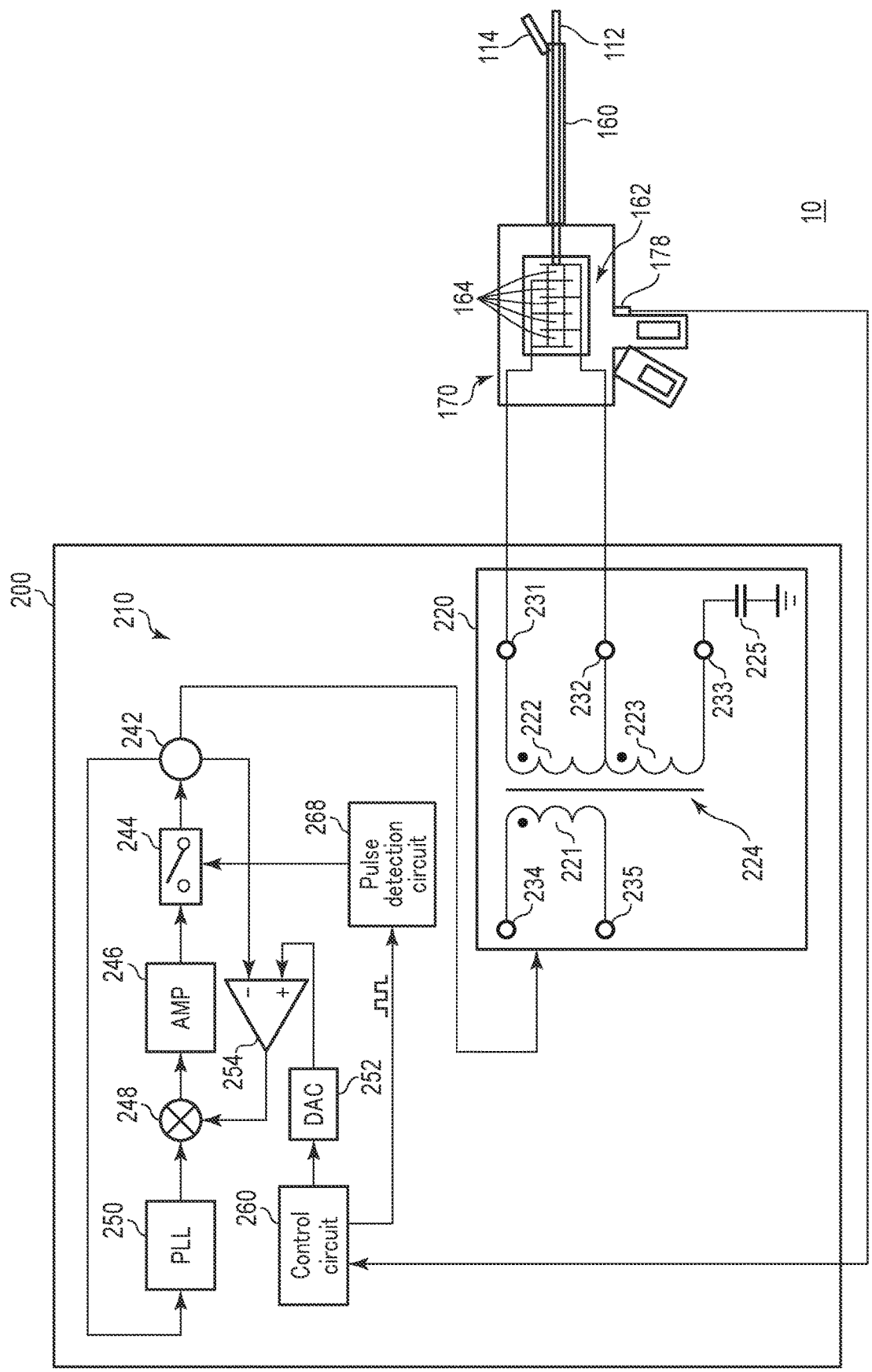
FIG. 2 is a schematic view showing an exemplary configuration of the ultrasonic surgical system according to the first embodiment.

FIG. 2 shows an exemplary circuit configuration of the ultrasonic surgical system 10. The operation unit 170 of the ultrasonic surgical instrument 100 is provided with the ultrasonic transducer 162. The ultrasonic transducer 162 includes a plurality of piezoelectric elements 164. Each of the piezoelectric elements 164 is sandwiched between electrodes mutually different in polarity. The piezoelectric elements 164 are stacked to form the ultrasonic transducer 162.

The generator 200 includes a drive circuit 210. The drive circuit 210 is a circuit for driving the ultrasonic transducer 162. In other words, the drive circuit 210 is a circuit which generates a voltage to be applied to the electrodes of the ultrasonic transducer 162. The generator 200 according to the present embodiment adopts a PLL control system as a resonance tracking system. The generator 200 further adopts a constant current control system as an amplitude control system.

The generator 200 includes a control circuit 260. The control circuit 260 controls the operation of each element in the generator 200, thereby controlling the operation of the ultrasonic surgical system 10. The control circuit 260 includes an integrated circuit such as, e.g., a Central Processing Unit (CPU), an Application Specific Integrated Circuit (ASIC), a Field Programmable Gate Array (FPGA), etc. The control circuit 260 may be formed of, for example, a single integrated circuit, or may be formed of a plurality of integrated circuits in combination. The operation of the control circuit 260 is executed in accordance with a program, etc., stored in a storage area within a memory circuit or a control circuit, for example.

For example, the control circuit 260 obtains an input to the output switch 178 of the ultrasonic surgical instrument 100. The control circuit 260 controls an output of the drive circuit 210 in accordance with an input to the output switch 178.

The drive circuit 210 includes a transformer unit 220. The transformer unit 220 includes a transformer 224. The transformer unit 220 boots a voltage, thereby outputting a necessary voltage. Outputs of the transformer unit 220 are input to the ultrasonic transducer 162. The transformer unit 220 has a further role of preventing a current containing a DC component from flowing between circuits of the generator 200 and circuits of the ultrasonic surgical instrument 100. Herein, the circuits of the ultrasonic surgical instrument 100 are those which come in contact with a patient. The circuits of the generator 200 are those which are connected to a commercial power source.

The drive circuit 210 includes a detection circuit 242, a relay 244, a power amplifier 246, a voltage control amplifier 248, a phase-locked loop (PLL) circuit 250, a DA converter (DAC) 252, a differential amplifier 254, and a pulse detection circuit 268.

The relay 244 is inserted between, for example, the power amplifier 246 and the transformer unit 220. The relay 244 switches ON/OFF an output line. When the output switch 178 is turned ON during use of the ultrasonic surgical instrument 100, the control circuit 260 detects this fact. At this time, the control circuit 260 detects whether or not the control circuit 260 is operating normally. When the control circuit 260 is operating normally, it outputs a pulse signal to the pulse detection circuit 268. On the other hand, when the control circuit 260 has an abnormality, it outputs no pulse. The pulse detection circuit 268 turns ON the relay 244 when a pulse is input from the control circuit 260. The pulse detection circuit 268 turns OFF the relay 244 when no pulse is input. Accordingly, when the control circuit 260 is operating normally, the drive circuit 210 operates. On the other hand, when the control circuit 260 has an abnormality, the drive circuit 210 does not operate.

Outputs of the voltage control amplifier 248 are input to the power amplifier 246. The power amplifier 246 amplifies an output of the voltage control amplifier 248, thereby adjusting a signal to be input to the transformer unit 220. The detection circuit 242 detects a voltage and a current, which are input from the power amplifier 246 to a primary coil of the transformer 224, as well as phases of these voltage and current.

The PLL circuit 250 is a circuit for tracking a resonance frequency of the ultrasonic transducer 162. The PLL circuit 250 performs resonance tracking by using a voltage phase signal and a current phase signal which are detected by the detection circuit 242. The PLL circuit 250 performs resonance tracking by controlling a phase difference between a voltage and a current in such a manner that the phase difference approximates to zero. Outputs of the PLL circuit 250 are input to the voltage control amplifier 248. The voltage control amplifier 248 is a multiplier. In addition to signals from the PLL circuit 250, signals from the differential amplifier 254 are input to the voltage control amplifier 248. The differential amplifier 254 compares a signal of a current magnitude obtained from the detection circuit 242 with a signal from the DAC 252.

The DAC 252 inputs to the differential amplifier 254 a signal relating to a magnitude of an output from the control circuit 260 to the ultrasonic transducer 162. When the output switch 178 is switched ON, the control circuit 260 outputs to the DAC 252 a digital signal relating to a target value of a magnitude of an output to the ultrasonic transducer 162. The DAC 252 converts a signal input from the control circuit 260 into an analog signal, thereby outputting the converted signal to the differential amplifier 254.

The differential amplifier 254 receives inputs of signals from the DAC 252 and signals from the detection circuit 242. The differential amplifier 254 compares a signal from the DAC 252 with a signal from the detection circuit 242. In other word, the differential amplifier 254 compares a control signal indicative of a target value of an output from the control circuit 260 with a present output detected by the detection circuit 242. The differential amplifier 254 outputs a comparison result to the voltage control amplifier 248.

The voltage control amplifier 248 multiplies an input from the PLL circuit 250 by an input from the differential amplifier 254. As a result, an output voltage is adjusted to have a magnitude indicated by the control circuit 260. Thus, a signal on which resonance tracking has been performed by the PLL circuit 250, which corresponds to an output adjusted to have a magnitude based on a control signal of the control circuit 260 using the voltage control amplifier 248 and the differential amplifier 254, is input to the power amplifier 246. The power amplifier 246 amplifies a signal, thereby outputting it to the transformer unit 220. The transformer unit 220 boosts an input voltage, thereby supplying a power to the ultrasonic transducer 162. In this manner, an energy is supplied as appropriate to the ultrasonic transducer 162

<Configuration of Transformer Unit>

The transformer unit 220 according to the present embodiment will be described in detail. The transformer unit 220 includes the transformer 224. The primary coil of the transformer 224 is formed of a first inductor 221. A power output from the power amplifier 246 is input to a first input contact 234 and a second input contact 235 at both ends of the primary coil via the detection circuit 242.

A secondary coil of the transformer 224 is formed of a second inductor 222 and a third inductor 223. The second inductor 222 is connected between a first contact 231 and a second contact 232. The third inductor 223 is connected between the second contact 232 and a third contact 233. Herein, the second inductor 222 and the third inductor 223 are configured in such a manner that the polarity of the first contact 231 with respect to the second contact 232 of the second inductor 222 and the polarity of the second contact 232 with respect to the third contact 233 of the third inductor 223 coincide with each other. The third contact 233 is grounded via a first capacitor 225.

The second inductor 222 and the third inductor 223 may be formed of a coil around which an electrical wire is continuously wound, in which both ends of this coil respectively correspond to the first contact 231 and the third contact 233, and the second contact 232 may be taken out midway between the first contact 231 and the third contact 233. In addition, the second inductor 222 and the third inductor 223 may be formed of separate coils. Considering the ease of manufacture, space saving, etc., it is preferable that the second inductor 222 and the third inductor 223 be formed of a coil around which an electrical wire is continuously wound.

Each of the first contact 231 and the second contact 232 at both ends of the second inductor 222 functions as an output terminal of the transformer unit 220. Namely, the electrodes of the ultrasonic transducer 162 are connected to the first contact 231 and the second contact 232. In particular, the output terminal is configured in such a manner that the second contact 232 is connected to one electrode arranged in the closest position to the first grasping piece 112, among the electrodes between which each piezoelectric element 164 is sandwiched in the ultrasonic transducer 162. Each of the first contact 231 and the second contact 232 functions as an output terminal of the transformer unit 220. Thus, the winding number of the second inductor 222 with respect to the winding number of the first inductor 221 is adjusted so as to correspond to the boosting ratio of the transformer unit 220.

The second contact 232 is a contact which is connected to the closest electrode to the first grasping piece 112 that comes in contact with a patient. This requires that a leakage current from the second contact 232 be maintained below a predetermined value. High vibration energy is required for treating a living tissue using ultrasonic vibration. This causes the transformer unit 220 configured to drive the ultrasonic transducer 162 to have a high output. Therefore, a leakage current from the second contact 232 tends to increase. Decrease of a leakage current from the second contact 232 requires strict adjustment for the transformer unit 220. Herein, the second contact 232 will be referred to as a patient side connection.

Figure 3:
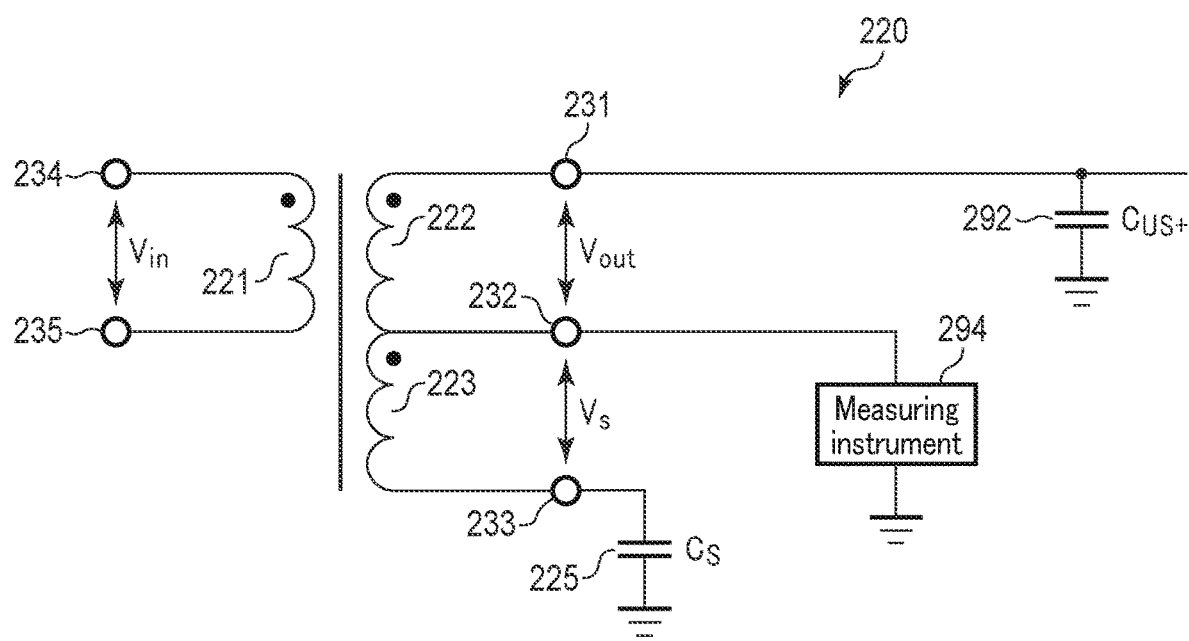
FIG. 3 is a schematic view showing an exemplary configuration of a transformer unit.

A relationship between the winding number of the third inductor 223 and a capacitance of the first capacitor 225 will be described with reference to FIG. 3. A stray capacitance 292 is present between the first contact 231 and ground due to a physical structure of a circuit. A capacitance of the stray capacitance 292 is set to $C_{us+}$. A potential difference between the first contact 231 and the second contact 232 at both ends of the second inductor 222 is set to $V_{out}$. A capacitance of the first capacitor 225 is set to $C_s$. A potential difference between the second contact 232 and the third contact 233 at both ends of the third inductor 223 is set to $V_s$. Under this condition, a potential of the second contact 232 as a patient side connection is determined by a relation with $V_s$, $C_s$, $V_{out}$, and $C_{us+}$. Accordingly, in the transformer unit 220, the winding number of the third inductor 223 and a capacitance of the first capacitor 225 are adjusted in such a manner that a potential of the second contact 232 is equal to or less than a predetermined value.

More specifically, each element of the transformer unit 220 is adjusted in such a manner that a potential of the second contact 232 as a patient side connection approximates to $0V_{pp}$ in conformity with IEC 60601-1 Standard, "Patient Leakage Current".

First, the first capacitor 225 having a predetermined capacitance is provided between the third contact 233 and ground. Herein, it is preferable that a capacitance of the first capacitor 225 be equal to or less than 100 pF. The reasons are as follows. Assume a malfunction state in which ground is connected to a power supply of 240 V of the generator 200. In this state also, a potential of the second contact 232 as a patient side connection is required to be equal to or less than a predetermined value. If a capacitance of the first capacitor 225 is too large, a potential of the second contact 232 exceeds a predetermined value in a malfunction state in which ground is connected to a power supply. To avoid this, a capacitance of the first capacitor 225 is required to be equal to or less than, e.g., 100 pF.

Next, under IEC 60601-1 Standard, "Patient Leakage Current", the winding number of the third inductor 223 is adjusted in such a manner that a patient leakage current measured by connecting the measuring instrument 294 to the second contact 232 is equal to or less than a predetermined value. For example, a low-frequency leakage current, which is measured using the measuring instrument 294 having a low-pass filter with a cutoff frequency of 1 kHz, for example, is required to be equal to or less than 10 µA.

Herein, since there are also requirements for the maximum voltage to be generated, it is preferable that voltage $V_s$ as a voltage of each end of the third inductor 223 be equal to or less than voltage $V_{out}$ as a voltage at each end of the second inductor 222. This is because it is desired that the maximum voltage generated within the generator 200 be voltage $V_{out}$, which is a voltage requested by the generator, and the other voltages be equal to or less than voltage $V_{out}$.

As a result of adjustment, each element during use exhibits a potential as described below. Assume that voltage $V_{in}$ to be applied between ends of the first inductor 221 as a primary coil has, for example, a peak-to-peak value of 56 Vpp, and a frequency of 47 kHz. Under this condition, voltage $V_{out}$ between ends of the second inductor 222, which is to be applied to the ultrasonic transducer 162, is equal to 1000 Vpp. Voltage $V_s$ as a voltage between ends of the third inductor 223 is equal to −1000 Vpp. A potential of the second contact 232 is equal to 0 Vpp.

A capacitance of the first capacitor 225 is adjusted to, for example, 37 to 39 pF. For example, a capacitance of the first capacitor 225 is adjusted to about 38 pF. Furthermore, an inductance of the second inductor 222 and an inductance of the third inductor 223 are each adjusted to, for example, 37 to 63 mH. For example, an inductance of the second inductor 222 and an inductance of the third inductor 223 are each adjusted to 50 mH.

According to the present embodiment, a potential of the second contact 232 as a patient side connection with respect to ground may be adjusted to be equal to or less than a predetermined value by adjusting a capacitance of the first capacitor 225 and the winding number of the third inductor 223.

In the above description, with a surgical instrument being the ultrasonic surgical instrument using ultrasonic waves, the generator that supplies a power to the ultrasonic transducer of the ultrasonic surgical instrument was explained as an example of a generator. However, the way of configuring the transformer unit as a countermeasure against a patient leakage current, such as described above, is applicable not only to the generator for the ultrasonic surgical instrument but also to other types. The technique described above is applicable to various types of generators for various types of energy conversion devices. Herein, the energy conversion devices indicate a device for converting energy into various types of energies. An ultrasonic transducer is one of various energy conversion devices. A heater which generates heat upon receipt of power supply is also one of various energy conversion devices. A motor which rotates a structural object upon receipt of power supply is also one of various energy conversion devices. The technique according to the present embodiment is applicable to a generator for a surgical instrument using a heater or a motor.

<Inspection Mode of Generator>

At medical sites, it is preferable that a medical engineer perform inspection of the generator 200. For this reason, the generator 200 includes an inspection mode in addition to a normal output mode in which energy is supplied for treatment to the ultrasonic surgical instrument 100.

The output mode and the inspection mode are switched under the control of the control circuit 260. When the control circuit 260 is a CPU, a program for the output mode and a program for the inspection mode are prepared as software. When the control circuit 260 is an FPGA, etc., a module for the output mode and a module for the inspection mode are prepared as hardware.

A user can switch between the normal mode and the inspection mode using a graphical user interface displayed on the touch screen 274 and input means such as the input unit 272 or the touch screen 274. In addition, a user can switch between ON and OFF of an output in the inspection mode, by using the graphical user interface and the input means.

Figure 4:
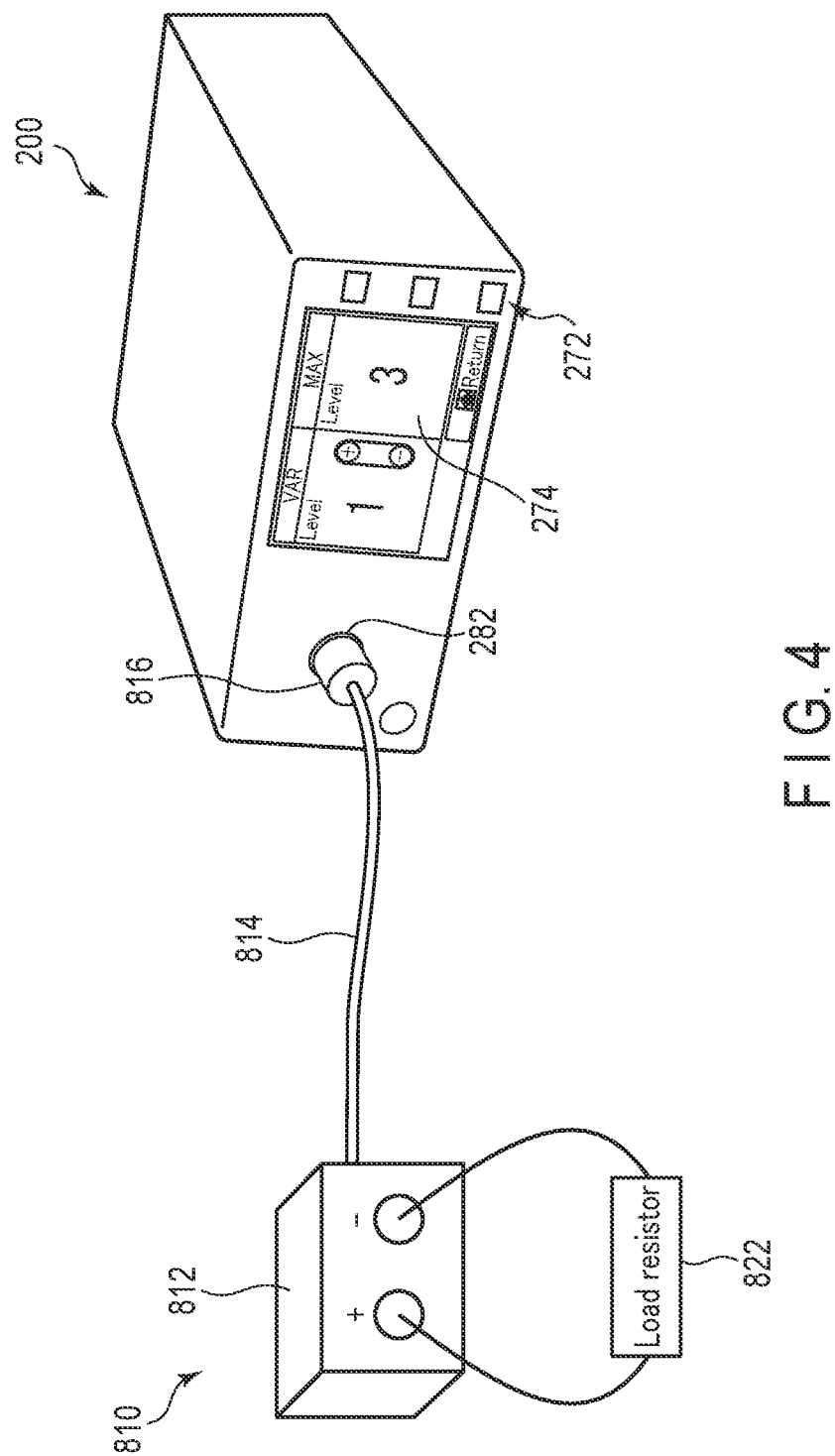
FIG. 4 is a schematic view showing an exemplary appearance of an ultrasonic surgical system in an inspection mode.

In the inspection mode, instead of the ultrasonic surgical instrument 100, an appropriate load resistor is connected to the generator 200. Herein, the socket 282 of the generator 200 is specially formed for the ultrasonic surgical instrument 100. Therefore, as shown in FIG. 4, an inspection adapter 810 is used in the inspection mode. That is, the inspection adaptor 810 includes a connection unit 812 configured for a load resistor 822 to be connected thereto. The connection unit 812 is provided with a plug 816 via a cable 814, in which the plug 816 is adapted to a shape of the socket 282 of the generator. The load resistor 822 is configured to be connected to the generator 200 through the use of the inspection adaptor 810.

In the inspection mode, the maximum output condition is simulated. For example, under the maximum output condition in which an output current is 0.9 App, an output voltage is 800 Vpp, and an output power is 90 W, a constant current of 0.9 App is output in the inspection mode. For this reason, a resistance value of the load resistor 822 is set to 800Ω.

As described above, a medical engineer can perform inspection of the generator 200 using the inspection mode, the inspection adaptor 810, and the load resistor 822.

Second Embodiment

A second embodiment will be described. Herein, differences from the first embodiment will be described. The same reference signs will be used to denote similar structural elements, and a description of such structural elements will be omitted. The first embodiment is one example of the ultrasonic surgical system 10 that performs treatment on a living tissue using an energy of ultrasonic vibration. The second embodiment relates to a surgical system 30 that performs treatment by applying a high-frequency current in addition to an energy of ultrasonic vibration, to a living tissue as a treatment target. When a high-frequency current is applied to a living tissue, the living tissue is heated with Joule heat. The living tissue is sealed, coagulated, cut, and so on with this heat in combination with ultrasonic vibration.

A surgical instrument 300 according to the present embodiment has a similar configuration to that of the ultrasonic surgical instrument 100 according to the first embodiment. That is, an operation unit 370 includes a main body 372, a fixed handle 374, a movable handle 376, and an output switch 378. The main body 372 has the proximal side to which an ultrasonic transducer 362 is connected. The main body 372 has the distal side in which a grasping portion 310 is provided via a shaft 360. The grasping portion 310 includes a first grasping piece 312 and a second grasping piece 314. The first grasping piece 312 is connected to the ultrasonic transducer 362, and vibrates in accordance with the vibration of the ultrasonic transducer 362. Portions of the first grasping piece 312 and the second grasping piece 314 come into contact with a living tissue, and in the present embodiment, these portions are provided with electrodes in order to apply a high-frequency current to the living tissue.

In the present embodiment, a power for the ultrasonic transducer 362 to vibrate is supplied to the surgical instrument 300. For this reason, the present embodiment uses the generator 200, which is the same as the generator 200 of the first embodiment. Furthermore, a high-frequency generator 400 is used in order to supply a high-frequency current to a living tissue via the grasping portion 310 of the surgical instrument 300. As in the case of the generator 200 for ultrasonic waves, the high-frequency generator 400 includes an input unit 512 and a touch screen 514. The generator 200 for ultrasonic waves and the high-frequency generator 400 are connected to each other. In the present embodiment, an output of the high-frequency generator 400 is output to the surgical instrument 300 via the generator 200. The surgical instrument 300 includes a cable 380 connected to the proximal end of the ultrasonic transducer 362 and a plug 382 provided in the proximal end of the cable 380. The surgical instrument 300 is connected to the socket 282 of the generator 200 via the cable 380 and the plug 382.

Figure 6:
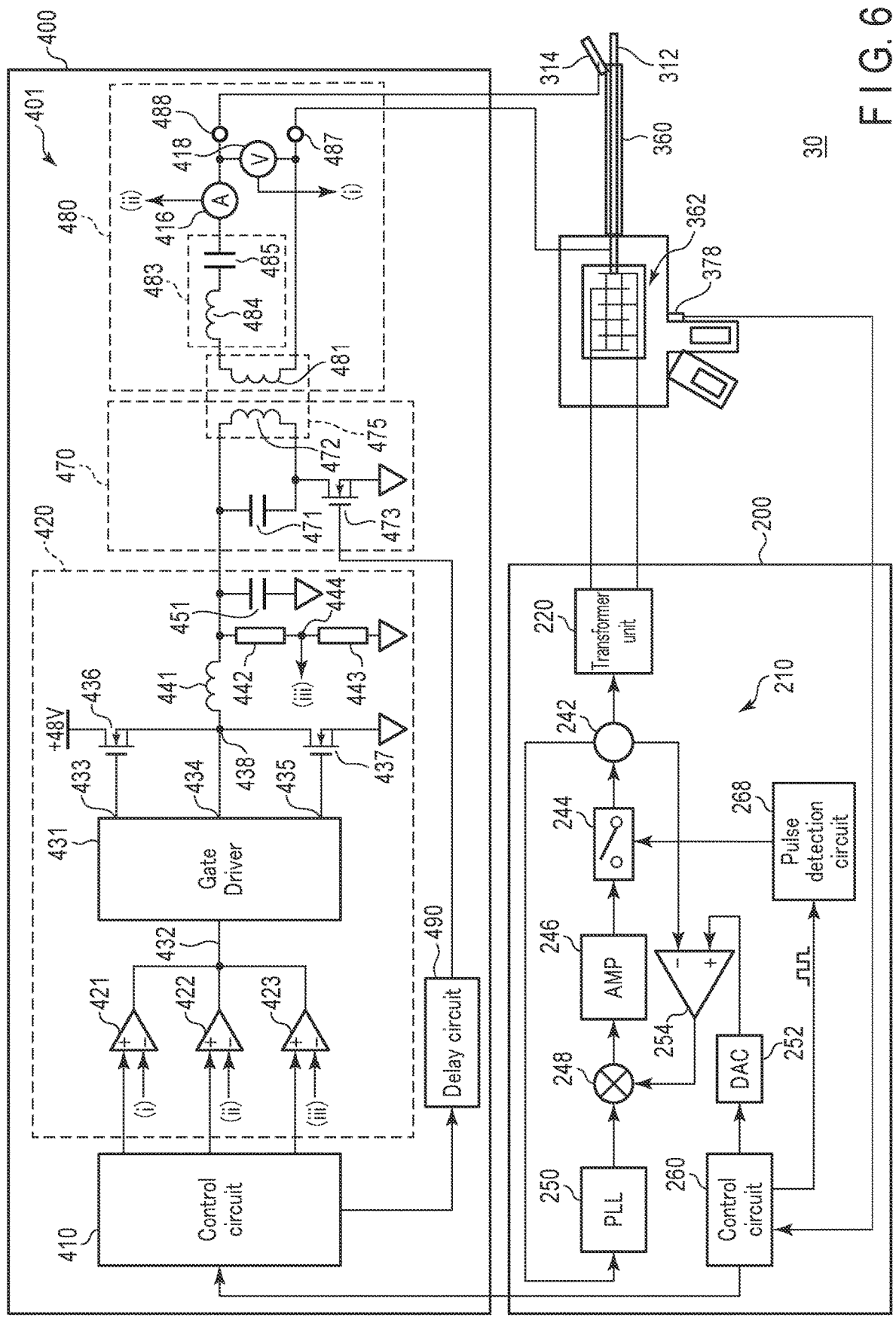
FIG. 6 is a schematic view showing an exemplary configuration of the surgical system according to the second embodiment.

FIG. 6 shows a circuit configuration of the surgical system 30. The surgical system 30 additionally includes a circuit for the high-frequency generator 400 in addition to the circuits included in the ultrasonic surgical system 10 shown in FIG. 2. Since the generator 200 for ultrasonic waves has the same configuration as that of the first embodiment, detailed description thereof will be omitted.

The high-frequency generator 400 includes a control circuit 410 and a drive circuit 401. The drive circuit 401 includes a High Voltage Power Supply (HVPS) 420 whose output is variable, a parallel resonance circuit 470, and a patient circuit 480. The control circuit 410 is composed of a CPU, an FPGA, an ASIC, etc. The control circuit 410 controls various operations of the high-frequency generator 400. The control circuit 410 is connected to the control circuit 260 of the generator 200 for ultrasonic waves. The control circuit 260 of the generator 200 for ultrasonic waves and the control circuit 410 of the high-frequency generator 400 exchange necessary information with each other. The control circuit 410 of the high-frequency generator 400 turns ON an output of the HVPS 420 based on the output switch 378 being turned ON. At this time, the control circuit 410 controls a magnitude of an output of the HVPS 420.

The HVPS 420 includes a DC/DC converter which utilizes a Class D amplifier. That is, the HVPS 420 includes a Class D amplifier including a gate driver 431, a first MOSFET 436, and a second MOSFET 437. An output node 438 of the Class D amplifier is connected to a high potential of, e.g., +48 V, via the first MOSFET 436. Herein, a drain electrode of the first MOSFET 436 is connected to the high potential. A source electrode of the first MOSFET 436 is connected to the output node 438. A gate electrode of the first MOSFET 436 is connected to a first terminal 433 of the gate driver 431. The output node 438 is connected to ground via the second MOSFET 437. Herein, a drain electrode of the second MOSFET 437 is connected to the output node 438. A source electrode of the second MOSFET 437 is connected to ground. A gate electrode of the second MOSFET 437 is connected to a second terminal 435 of the gate driver 431. The output node 438 is connected to a terminal 434 for potential measurements of the gate driver 431.

With the gate driver 431, the first MOSFET 436 and the second MOSFET 437 are controlled in such a manner as to be alternatively turned ON, so that a potential of the output node 438 is alternatively switched between a high potential and a low potential. Namely, this Class D amplifier outputs square waves in accordance with a drive frequency of the gate driver 431. The Class D amplifier adjusts an output using a pulse width modulation (PWM).

An output of the output node 438 is input to a low-pass filter formed of a fourth inductor 441 and a second capacitor 451. This low-pass filter operates as a passive integrator. A potential stabilized by the fourth inductor 441 and the second capacitor 451 is output as an output of the HVPS 420. A value concerning an output potential of the HVPS 420 is obtained in a manner described below. Namely, the first resistor 442 and the second resistor 443 are connected in series between an output of the HVPS 420 and ground. A reference potential acquisition node 444 is provided between the first resistor 442 and the second resistor 443. A potential of the reference potential acquisition node 444 is taken out as a reference potential, as represented by (iii) in FIG. 6.

An input signal to the gate driver 431 determines an output frequency thereof, and is input via an input line 432. To the input line 432, outputs of a first differential amplifier 421, a second differential amplifier 422, and a third differential amplifier 423 are connected. The first differential amplifier 421 receives inputs of a controlling value of an output voltage output from the control circuit 410, and a value concerning a voltage value of a voltage to be applied between a first output terminal 487 and a second output terminal 488, represented by (i) in FIG. 6. Herein, the first output terminal 487 and the second output terminal 488 form an output terminal of the drive circuit 401. That is, a voltage value of an output voltage is fed back. The second differential amplifier 422 receives inputs of a controlling value of an output current output from the control circuit 410, and a value concerning a current value of a current flowing through second output terminal 488, represented by (ii) in FIG. 6. That is, a current value of an output current is fed back. The third differential amplifier 423 receives inputs of a controlling value of an output voltage of the HVPS 420 output from the control circuit 410, and a value concerning a reference potential relating to an output voltage of the HVPS 420, represented by (iii) in FIG. 6. That is, a value relating to a voltage value of an output voltage of the HVPS 420 is fed back. An input signal to the input line 432, which determines a drive frequency of the gate driver 431, is equal to, for example, the product of an output of the first differential amplifier 421, an output of the second differential amplifier 422, and an output of the third differential amplifier 423. In this case, when all the first differential amplifier 421, the second differential amplifier 422, and the third differential amplifier 423 produce high-level outputs, an input signal to the input line 432 is at a high level. The gate driver 431 operates based on a PWM signal input to the input line 432 described above.

An output of the HVPS 420 is input to the parallel resonance circuit 470. The parallel resonance circuit 470 includes a third capacitor 471 and a fifth inductor 472 which are mutually connected in parallel. The third capacitor 471 and the fifth inductor 472 form a parallel resonance circuit that has one end connected to an output of the HVPS 420. The other end of the parallel resonance circuit is grounded via the third MOSFET 473. Herein, a drain electrode of the third MOSFET 473 is connected to the parallel circuit. A source electrode of the third MOSFET 473 is connected to ground. A gate electrode of the third MOSFET 473 is connected to the control circuit 410 via a delay circuit 490.

The parallel resonance circuit 470 repeats charging and discharging by using an output power of the HVPS 420 in accordance with switching between ON and OFF of the third MOSFET 473. A switching frequency for switching between ON and OFF of the third MOSFET 473 is set to a drive frequency of a high-frequency power output from the surgical instrument 300.

The parallel resonance circuit 470 and the patient circuit 480 are connected together via a transformer 475. The transformer 475 is formed of the fifth inductor 472 as a primary coil and a sixth inductor 481 as a secondary coil. That is, the fifth inductor 472 is shared by the parallel resonance circuit 470 and the transformer 475. The transformer 475 boosts an output voltage of the parallel resonance circuit 470. The transformer 475 further functions to prevent a current containing a DC component from flowing between circuits of the high-frequency generator 400 and circuits of the surgical instrument 300. Herein, the circuits of the surgical instrument 300 are those which come in contact with a patient. The circuits of the high-frequency generator 400 are those which are connected to a commercial power source.

The patient circuit 480 includes a series resonance circuit 483. The series resonance circuit 483 is a circuit in which a seventh inductor 484 and a fourth capacitor 485 are connected in series. The sixth inductor 481 that forms a secondary coil of the transformer 475 has one end connected to the first output terminal 487. The other end of the sixth inductor 481 is connected to one end of the seventh inductor 484. The other end of the seventh inductor 484 is connected to one end of the fourth capacitor 485. The other end of the fourth capacitor is connected to the second output terminal 488 via an ammeter 416. The ammeter 416 may be arranged at a side close to the first output terminal 487, instead of at a side close to the second output terminal 488.

The first output terminal 487 is connected to an electrode provided in the first grasping piece 312 of the surgical instrument 300. The second output terminal 488 is connected to an electrode provided in the second grasping piece 314 of the surgical instrument 300. When treatment is performed, a living tissue as a treatment target is sandwiched between the first grasping piece 312 and the second grasping piece 314. At this time, electrodes of the first grasping piece 312 and the second grasping piece 314 come into contact with a living tissue. That is, the first output terminal 487 and the second output terminal 488 are connected to each other with a living tissue interposed therebetween.

The series resonance circuit 483 formed of the seventh inductor 484 and the fourth capacitor 485 function as a band pass filter which transmits signals within a specific band of input high-frequency signals. Herein, a band allowed to transmit is set to a band which contains a drive frequency of the surgical instrument 300. A high-frequency signal input to the series resonance circuit 483 is converted into a sinusoidal signal by the series resonance circuit 483, thereby being applied to a living tissue via the treatment portion 110.

The ammeter 416 inserted between the series resonance circuit 483 and the second output terminal 488 detects a current output from the second output terminal 488. As described above, a measured value of the ammeter 416 is input to the second differential amplifier 422, as represented by (ii) in FIG. 6. That is, a signal indicative of an output current of a high-frequency power is input to the second differential amplifier 422. In addition, the voltmeter 418 configured to detect a voltage to be applied between the first output terminal 487 and the second output terminal 488 is provided between the first output terminal 487 and the second output terminal 488. As described above, a measured value of voltmeter 418 is input to the first differential amplifier 421, as represented by (i) in FIG. 6. That is, a signal indicative of an output voltage of a high-frequency power is input to the first differential amplifier 421.

In treatment, a user operates the surgical instrument 300 to grasp a living tissue as a treatment target with the first grasping piece 312 and the second grasping piece 314. In this state, a user turns ON the output switch 378. This causes the drive circuit 210 of the generator 200 for ultrasonic waves to supply a power to the ultrasonic transducer 362 of the surgical instrument 300 under the control of the control circuit 260. As a result, the first grasping piece 312 vibrates at a frequency of ultrasonic waves, thereby performing treatment on a living tissue. Along with this, the drive circuit 401 of the high-frequency generator 400 applies a high-frequency voltage between the first grasping piece 312 and the second grasping piece 314 under the control of the control circuit 410. This causes a high-frequency current to flow through a living tissue, so that treatment is performed thereon.

When the output switch 378 is turned OFF or after a predetermined energy output is performed, the generator 200 for ultrasonic waves and the high-frequency generator 400 stop their outputs. With that, treatment on a living tissue is completed.

<Re: Delay Circuit>

The delay circuit 490 included in the drive circuit 401 of the high-frequency generator 400 will be described. Under the control of the high-frequency generator 400, the control circuit 410 inputs to the HVPS 420 a control signal for switching between ON and OFF of an output of the HVPS 420. More specifically, a control signal input from the control circuit 410 to each of the first differential amplifier 421, the second differential amplifier 422, and the third differential amplifier 423 is switched between ON and OFF. When a control signal input to the HVPS 420 is ON, the HVPS 420 outputs a DC voltage of a controlled voltage.

Furthermore, the control circuit 410 inputs to the parallel resonance circuit 470 a control signal for switching between ON and OFF of an output. More specifically, when an output is ON, the control circuit 410 outputs to the third MOSFET 473 a pulse wave having a drive frequency of the surgical instrument 300. When an output is OFF, the aforementioned pulse wave is not input. When an output of the HVPS 420 is ON and the control circuit 410 inputs a pulse wave to the third MOSFET 473, the parallel resonance circuit 470 outputs an AC signal in accordance with a frequency of the pulse signal.

Herein, assume that a time when an output of a control signal from the control circuit 410 to the HVPS 420 is switched from ON to OFF coincides with a time when an input of a pulse wave from the control circuit 410 to the parallel resonance circuit 470 is switched from ON to OFF.

When the third MOSFET 473 is turned OFF, charges stored in the second capacitor 451 remain for a while. If the HVPS 420 is turned ON again in this state, there is a risk that a transient voltage peak noise will be imposed on an output voltage of the HVPS 420. This causes a risk of adversely affecting components such as the MOSFET of the HVPS 420. To avoid this risk, the present embodiment is configured in such a manner that charges stored in the second capacitor 451 are charged immediately.

Figure 7:
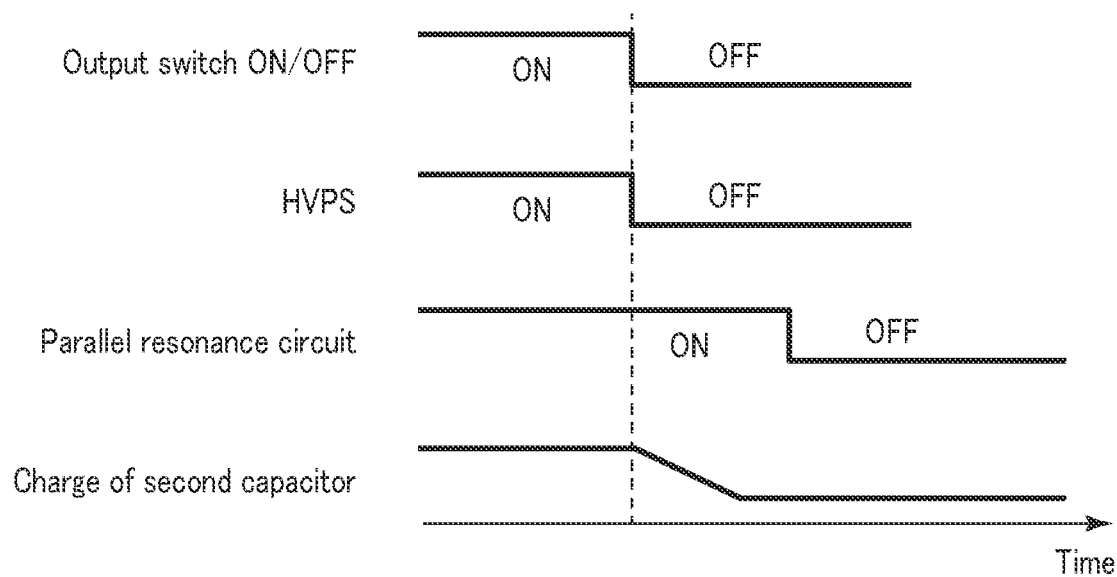
FIG. 7 is a timing chart showing how each element behaves when an output is switched from ON to OFF.

In the present embodiment, the delay circuit 490 is provided between the control circuit 410 and the third MOSFET 473 of the parallel resonance circuit 470. As a result, when an output is switched to OFF, each element behaves as shown in a timing chart in FIG. 7. Namely, when the output switch 378 is switched from ON to OFF, a control signal input to the HVPS 420 is also switched from ON to OFF. On the other hand, an input of a pulse wave to the parallel resonance circuit 470 is switched to OFF in a delayed fashion. As a result, by the parallel resonance circuit 470 being operating, charges stored in the second capacitor 451 are discharged quickly. A control signal to the parallel resonance circuit 470 is switched to OFF after charges stored in the second capacitor 451 are discharged. This makes it difficult for the HVPS 420 to be turned ON again with charges being stored in the second capacitor 451, so that components are prevented from having defects.

Figure 8:
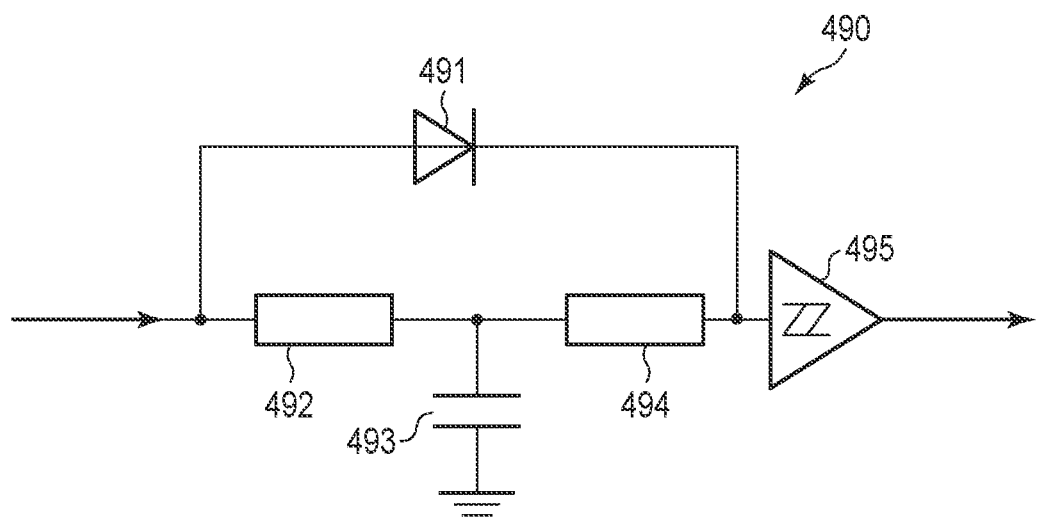
FIG. 8 is a schematic view showing an exemplary configuration of a delay circuit.

One example of the delay circuit 490 is shown in FIG. 8. The delay circuit 490 includes a time constant circuit, a diode, and a Schmitt trigger circuit. Namely, input end of the delay circuit 490 is connected to one end of a third resister 492. The other end of the third resistor 492 is connected to one end of a fifth capacitor 493. The other end of the fifth capacitor 493 is grounded. The other end of the third resistor 492 is connected to one end of a fourth resistor 494. The other end of the fourth resistor 494 is connected to an input end of a Schmitt trigger circuit 495. A diode 491 is inserted between an input end of the third resistor 492 and an input end of the Schmitt trigger circuit 495 in such a manner as to set a forward direction to a direction from the input end of the third resistor 492 to the input end of the Schmitt trigger circuit 495.

The diode 491 is inserted in order to vary a delay time between a time when the parallel resonance circuit 470 is switched from OFF to ON and a time when the parallel resonance circuit 470 is switched from ON to OFF. Namely, a current flows through the diode 491 when the parallel resonance circuit 470 is switched from OFF to ON, whereas a current flows through the third resistor 492 and the fifth capacitor 493 when the parallel resonance circuit 470 is switched from ON to OFF. In this manner, the adjustment is performed in such a manner that a time when the parallel resonance circuit 470 is switched from ON to OFF is delayed as appropriate.

<Modification of Delay Circuit>

In the drive circuit 401 described in the above, the delay circuit 490 prevents charges from remaining in the second capacitor 451 when an output is turned OFF. However, even without the delay circuit 490, ON/OFF of an output may be adjusted under the control of the control circuit 410.

Figure 9:
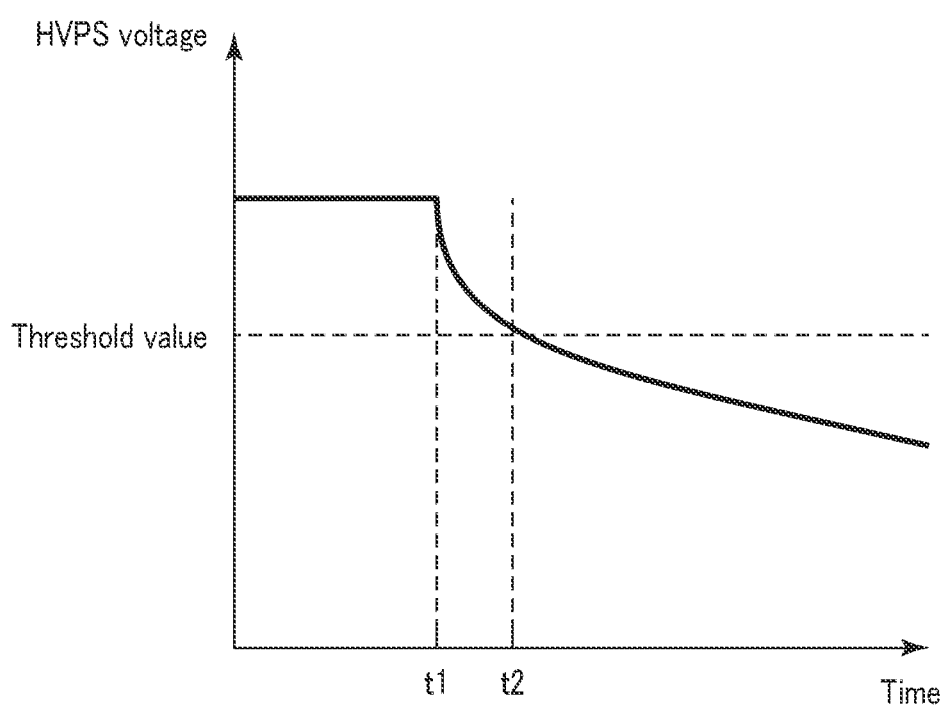
FIG. 9 is a view for illustrating output control by a control circuit.

For example, the control circuit 410 obtains an output voltage value of the HVPS 420, which is generated by charges remaining in the second capacitor 451. FIG. 9 shows the variation in an output voltage of the HVPS 420 with respect to the elapsed time. Assume that a control signal to the HVPS 420 is switched from ON to OFF at time t1. In this case, a voltage of the HVPS 420 is gradually decreased by charges stored in the second capacitor 451 being discharged.

The control circuit 410 detects the fact that an output voltage of the HVPS 420 has fallen below a threshold value. The control circuit 410 enables the HVPS 420 to be turned ON after its output voltage falls below a threshold value. As described above, under the control of the control circuit 410, an output of the HVPS 420 is prevented from being switching ON again while the second capacitor 451 is storing charges.

As a matter of course, the control circuit 410 may perform the control described above in the presence of the delay circuit 490.

<Re: Feedback Signal of HVPS>

As described above, an input signal to the input line 432, which determines a drive frequency of the gate driver 431 of the HVPS 420, is based on outputs of the first differential amplifier 421, the second differential amplifier 422, and the third differential amplifier 423. The output voltage (i), the output current (ii), and the reference potential relating to an output voltage of the HVPS 420 (iii) are respectively fed back to the first differential amplifier 421, the second differential amplifier 422, and the third differential amplifier 423.

The output voltage (i) to be input to the first differential amplifier 421 is a voltage obtained by converting a high-frequency output voltage into a DC voltage; however, the output voltage (i) includes a ripple of a high-frequency component. A frequency of this high-frequency ripple is equivalent to an output frequency and is, for example, about 350 to 400 kHz. Similarly, the output current (ii) to be input to the second differential amplifier 422 is a voltage obtained by converting a high-frequency output current into a DC current; however, the output current (ii) includes a ripple of a high-frequency component. A frequency of this high-frequency ripple is equivalent to an output frequency and is, for example, about 350 to 400 kHz. Furthermore, the reference potential (iii) relating to an output voltage of the HVPS 420 is affected by the resonance circuit in a subsequent stage and includes a ripple of a high-frequency component.

Therefore, signals to be input from the input line 432 to the gate driver 431 also include signals ranging from 350 to 400 kHz. As a result, a drive frequency of the gate driver 431 also range from 350 to 400 kHz. On the other hand, when the first the first MOSFET 436 and the second MOSFET 437 are driven with such a high frequency, a switching loss increases in the first MOSFET 436 and the second MOSFET 437. That is, the first MOSFET 436 and the second MOSFET 437 are heated to decrease a power supply efficiency of the HVPS 420. It is preferable that a drive frequency of each of the first MOSFET 436 and the second MOSFET 437 be about 100 kHz, for example.

Figure 10:
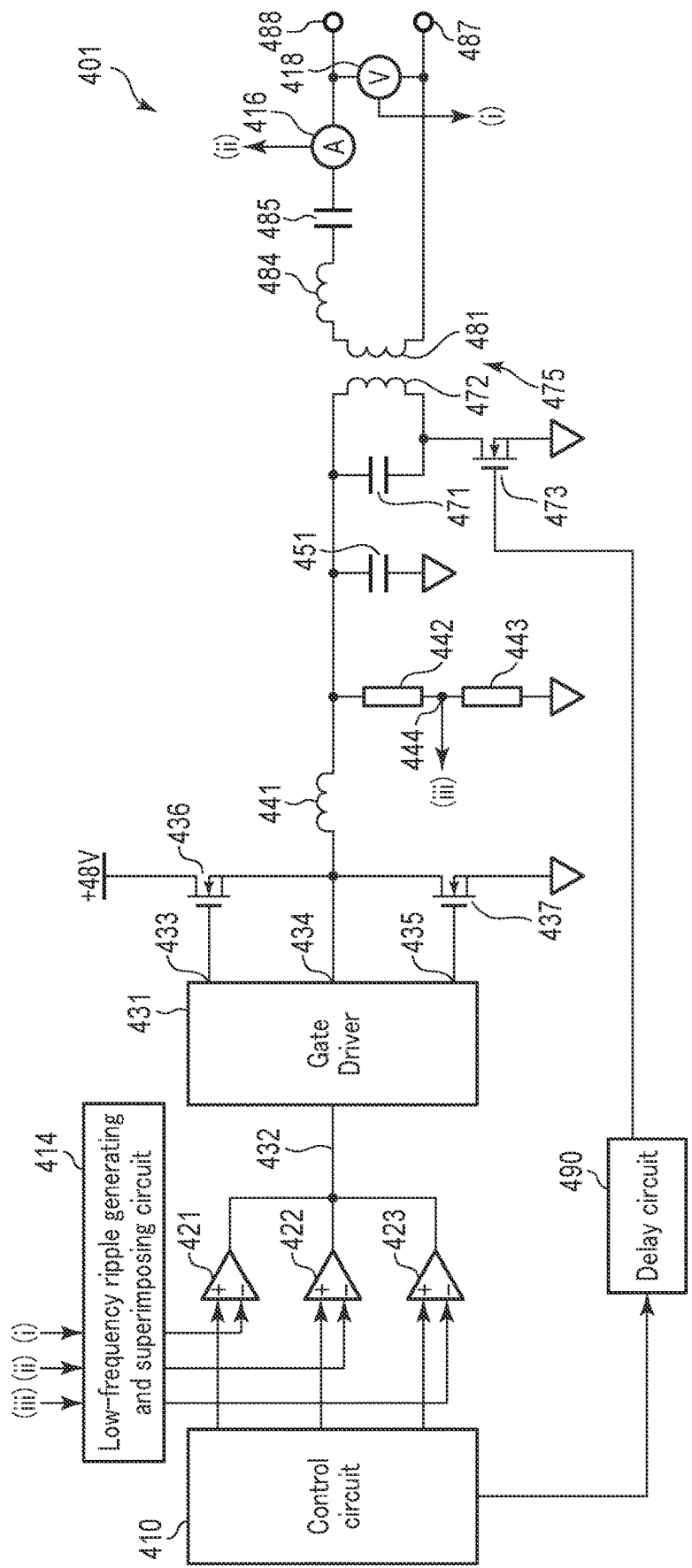
FIG. 10 is a schematic view showing an exemplary configuration of a drive circuit according to a modification of the second embodiment.

Accordingly, in the modification of the second embodiment, the drive circuit 401 is provided with a low-frequency ripple generating and superimposing circuit 414, as shown in FIG. 10. The low-frequency ripple generating and superimposing circuit 414 generates a low-frequency ripple which has a frequency lower than an output frequency of a high-frequency output and larger than a high-frequency ripple. The low-frequency ripple generating and superimposing circuit 414 further superimposes the generated low-frequency ripple on the output voltage (i), the output current (ii), and the reference potential (iii).

Figure 11A:
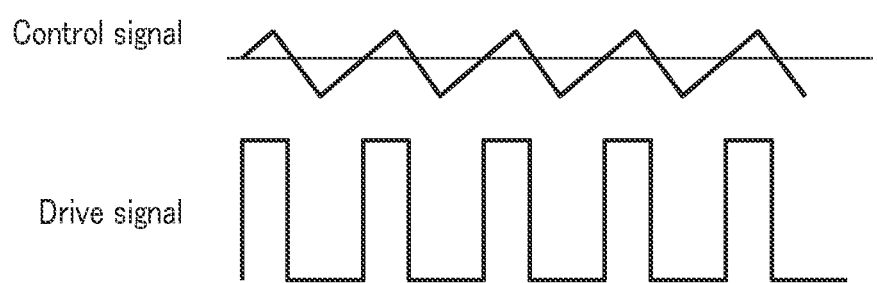
FIG. 11A is a view for illustrating a relationship between a high-frequency ripple of a control signal and a drive signal.
Figure 11B:
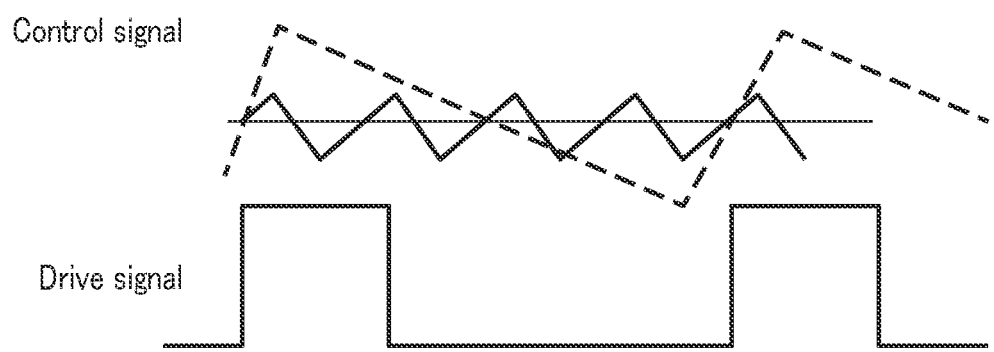
FIG. 11B is a view for illustrating a relationship between a control signal on which a low-frequency ripple is superimposed and a drive signal.

For example, when a low-frequency ripple is not superimposed, as shown in FIG. 11A, a control signal input to the input line 432 includes a high-frequency ripple in a range, for example, from 350 to 400 kHz. As a result, a drive signal of the gate driver 431 has a high frequency in a range, for example, from 350 to 400 kHz. On the other hand, when the low-frequency ripple generating and superimposing circuit 414 is provided to superimpose a low-frequency ripple on the output voltage (i), the output current (ii), and the reference potential (iii), as shown in FIG. 11B, a low-frequency ripple represented by the dashed-dotted line is superimposed on a control signal represented by the solid line. As a result, a drive signal of the gate driver 431 has a relatively low frequency, such as, e.g., 100 kHz. In this manner, a switching loss is decreased in the first MOSFET 436 and the second MOSFET 437. Furthermore, when a drive frequency is too low, coil noise is caused. Coil noise is prevented by controlling a drive frequency to be moderately high.

<First Example of Low-Frequency Ripple Generating Circuit>

Figure 12:
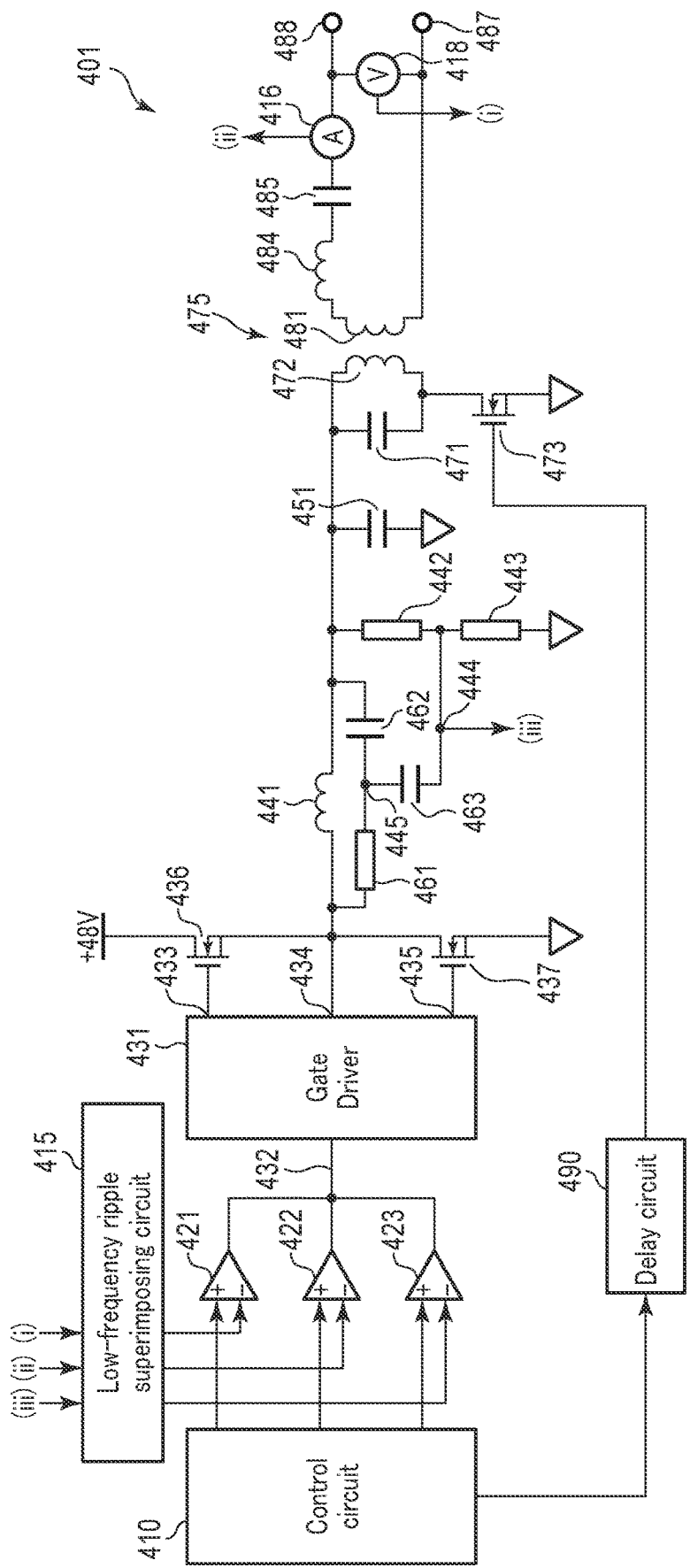
FIG. 12 is a schematic view showing an exemplary configuration of a drive circuit including a low-frequency ripple generating circuit in a first example.

FIG. 12 shows an example of the low-frequency ripple generating circuit (low-frequency triangular wave ripple circuit). In this example, a fifth resistor 461 and a sixth capacitor 462 are inserted in sequence, in parallel with the fourth inductor 441, and a signal of a low frequency is obtained from a low-frequency ripple acquisition node 445 between the fifth resistor 461 and the sixth capacitor 462. Namely, a signal relating to a voltage value of an output voltage of the HVPS 420, on which a low-frequency ripple component is superimposed as the reference potential (iii), is obtained. In this manner, a low-frequency ripple is generated with the fifth resistor 461 and the sixth capacitor 462. By inserting a seventh capacitor 463 between the low-frequency ripple acquisition node 445 and the reference potential acquisition node 444, a DC component of a signal input from the low-frequency ripple acquisition node 445 to the reference potential acquisition node 444 may be blocked.

The reference potential (iii) including the low-frequency ripple obtained in a manner described above is set to a feedback signal to be input to the third differential amplifier 423. Furthermore, the low-frequency ripple superimposing circuit 415 superimposes a low-frequency ripple included in the reference potential (iii) on the output voltage (i) and the output current (ii). The low-frequency ripple superimposing circuit 415 inputs to the first differential amplifier 421 the output voltage (i) on which the low-frequency ripple is superimposed, as a feedback signal. The low-frequency ripple superimposing circuit 415 inputs to the second differential amplifier 422 the output current (ii) on which the low-frequency ripple is superimposed, as a feedback signal.

As described above, a low-frequency ripple to be superimposed on a feedback signal can be generated using an output of the Class D amplifier.

<Second Example of Low-Frequency Ripple Generating Circuit>

FIG. 13 shows an example of the low-frequency ripple generating circuit (sinusoidal ripple circuit). In this example, in addition to the circuits shown in FIG. 12, a subsequent circuit is provided. Namely, in order to block a high-frequency component which flows backward from the parallel resonance circuit 470, a low-pass filter is inversely provided in an output portion of the HVPS 420. That is, an eighth inductor 465 is inserted between on output end of the fourth inductor 441 and an input end of the second capacitor 451. Furthermore, one end of the eighth capacitor 466 is connected between an output end of the fourth inductor 441 and an input end of the eighth inductor 465. The other end of the eighth capacitor 466 is grounded. The eighth inductor 465 and the eighth capacitor 466 block a high-frequency component of a sinusoidal signal which flows from the parallel resonance circuit 470 to the reference potential acquisition node 444. As a result, in the reference potential acquisition node 444, the reference potential (iii) on which a sinusoidal ripple of a low frequency is superimposed is obtained.

The thus obtained reference potential (iii) on which a low-frequency ripple is superimposed is set to a feedback signal to be input to the third differential amplifier 423. Furthermore, the low-frequency ripple superimposing circuit 415 superimposes a low-frequency ripple, on which the reference potential (iii) is superimposed, on the output voltage (i) and the output current (ii). The low-frequency ripple superimposing circuit 415 inputs to the first differential amplifier 421 the output voltage (i) on which the low-frequency ripple is superimposed, as a feedback signal. The low-frequency ripple superimposing circuit 415 inputs to the second differential amplifier 422 the output current (ii) on which the low-frequency ripple is superimposed, as a feedback signal.

As described above, a low-frequency ripple to be superimposed on a feedback signal can be generated using a backward flow component from the parallel resonance circuit 470.

Additional advantages and modifications will readily occur to those skilled in the art. Therefore, the embodiment in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A generator comprising:
a first inductor formed as a primary coil of a transformer;
a second inductor formed as a first secondary coil of the transformer, the second inductor being connected between a first contact and a second contact, the first contact and the second contact each being connected to a surgical instrument;
a third inductor formed as a second secondary coil of the transformer continuously connected with the first secondary coil of the second inductor, the third inductor being connected between the second contact and a third contact, a polarity of the second contact with respect to the third contact coinciding with a polarity of the first contact with respect to the second contact of the second inductor; and
a capacitor connected between the third contact and ground, an inductance of the third inductor and a capacitance of the capacitor being adjusted to set a potential of the second contact to be equal to or less than a predetermined value.

2. The generator according to claim 1, wherein the capacitance of the capacitor is equal to or less than 100 pF.

3. The generator according to claim 1, wherein the generator includes a power supply that is configured to supply a voltage to the first inductor, and the generator is configured to control a voltage between the second contact and the third contact to be equal or less than a voltage between the first contact and the second contact.

4. The generator according to claim 1, wherein the capacitance of the capacitor is in a range of 37 to 39 pF.

5. The generator according to claim 1, wherein an inductance of the second inductor and an inductance of the third inductor are each in a range of 37 to 63 mH.

6. The generator according to claim 1, further comprising a power supply configured to supply power to an ultrasonic transducer, a heater, or a motor, each being configured to serve as an energy conversion device included in the surgical instrument.

7. A surgical system comprising:
   a surgical instrument; and
   a generator including:
   a first inductor formed as a primary coil of a transformer;
   a second inductor formed as a first secondary coil of the transformer continuously connected with the first secondary coil of the second inductor the second inductor being connected between a first contact and a second contact, the first contact and the second contact each being connected to a surgical instrument;
   a third inductor formed as a second secondary coil of the transformer, the third inductor being connected between the second contact and a third contact, a polarity of the second contact with respect to the third contact coinciding with a polarity of the first contact with respect to the second contact of the second inductor; and
   a capacitor connected between the third contact and ground, and an inductance of the third inductor and a capacitance of the capacitor are adjusted to set a potential of the second contact to be equal to or less than a predetermined value.

* * * * *